(12) United States Patent
White et al.

(10) Patent No.: US 9,316,661 B2
(45) Date of Patent: Apr. 19, 2016

(54) DEVICES, SYSTEMS AND METHODS FOR LOADING SAMPLES

(75) Inventors: Nigel Thornton Hopley White, Dorking (GB); Steven Edward Liebold, Palatine, IL (US); Gary Vincent Millard, Lisle, IL (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 408 days.

(21) Appl. No.: 13/607,120

(22) Filed: Sep. 7, 2012

(65) Prior Publication Data

US 2013/0220037 A1 Aug. 29, 2013

Related U.S. Application Data

(60) Provisional application No. 61/603,224, filed on Feb. 24, 2012.

(51) Int. Cl.
*G01N 1/00* (2006.01)
*G01N 35/10* (2006.01)

(52) U.S. Cl.
CPC ........ *G01N 35/1004* (2013.01); *G01N 35/1016* (2013.01); *G01N 35/1095* (2013.01)

(58) Field of Classification Search
CPC . G01N 1/38; G01N 35/1004; G01N 35/1016; G01N 35/1095; B01L 2200/027; B01L 2300/0864
USPC ........................................................ 73/864.81
See application file for complete search history.

(56) References Cited

U.S. PATENT DOCUMENTS

| 5,410,403 A | 4/1995 | Wells |
| 6,902,702 B1 | 6/2005 | Winegarden |
| 7,572,638 B2 * | 8/2009 | Pressman et al. ............... 436/47 |
| 2003/0138947 A1 | 7/2003 | Gong |
| 2004/0092033 A1 | 5/2004 | Gustafson |
| 2007/0231206 A1* | 10/2007 | Nagai et al. ..................... 422/63 |
| 2008/0223463 A1 | 9/2008 | Zantl |
| 2009/0035873 A1* | 2/2009 | Shibata ......................... 436/179 |
| 2010/0055772 A1* | 3/2010 | Nagai et al. ................. 435/287.3 |
| 2010/0216224 A1* | 8/2010 | Okubo et al. ............. 435/286.5 |
| 2010/0247379 A1* | 9/2010 | Schmidt .......................... 422/67 |
| 2011/0076755 A1* | 3/2011 | Ebi et al. .................... 435/287.3 |
| 2011/0108719 A1 | 5/2011 | Ford |
| 2011/0184570 A1* | 7/2011 | Nakanishi et al. ............ 700/285 |
| 2012/0031175 A1* | 2/2012 | Ikeda et al. .................. 73/61.59 |

FOREIGN PATENT DOCUMENTS

JP 2003083851 3/2003

OTHER PUBLICATIONS

IPRP for PCT/US13/27280.
European Search Report for EP13752275.1 mailed on Aug. 19, 2015.

* cited by examiner

*Primary Examiner* — Hezron E Williams
*Assistant Examiner* — Rodney T Frank
(74) *Attorney, Agent, or Firm* — Rhodes IP PLC; Chistopher R Rhodes

(57) ABSTRACT

Certain embodiments described herein are directed to devices and system that can be used to fill a sample cell. In some examples, the system can be configured with a pressure device configured to provide a negative pressure to accelerate filling of the cell with the sample. In some embodiments, the negative pressure can be used to fill a flow cell at a selected fill rate.

21 Claims, 7 Drawing Sheets

| Sample Designation | Sample Details | Viscosity @ 40°C (cSt) | Fill Mode | Total fill time (Injection to cell full) (s) |
|---|---|---|---|---|
| Heptane | VWR Heptane tech grade (mixture of isomers) | 0.51 | Direct | 7.23 |
| VISC10 | VHG Visc10 Viscosity Reference Standard | 8.848 | Direct | 7.23 |
| VISC30 | VHG Visc30 Viscosity Reference Standard | 30.92 | Vac Assist | 7.49 |
| 15W40 | Halfords 15W40 Mineral Motor Oil | 120 (est.) | Vac Assist | 9.27 |
| VISC180 | Cannon S200 General Purpose Viscosity Standard | 180 | Vac Assist | 10.60 |
| VISC300 | VHG Visc300 Viscosity Reference Standard | 314.9 | Vac Assist | 12.64 |
| ISO460 | Shell Omala ISO 460 | 460 | Vac Assist | 19.36 |
| ISO680 | Shell Omala ISO 680 | 680 | Vac Assist | 22.07 |

FIG. 8

DEVICES, SYSTEMS AND METHODS FOR LOADING SAMPLES

PRIORITY APPLICATION

This application claims priority to, and the benefit of, U.S. Provisional Application No. 61/603,224 filed on Feb. 24, 2012, the entire disclosure of which is hereby incorporated herein by reference.

TECHNOLOGICAL FIELD

Certain features, aspects and embodiments are directed to devices that can be used in loading samples. In particular, certain embodiments described herein are directed to devices, systems and methods that can be used to load samples into a chamber.

BACKGROUND

In most analytical systems, samples are loaded into an instrument for measurement. In some instances, samples with different viscosities may be loaded into the instrument for analysis.

SUMMARY

In one aspect, a system comprising a sample introduction device, a flow cell fluidically coupled to the sample introduction device and configured to receive sample from the sample introduction device through a fluid inlet of the flow cell, a sensor coupled to the fluid inlet of the flow cell and configured to determine the time of arrival of sample at the fluid inlet of the flow cell, a valve fluidically coupled to the flow cell, and a pressure device fluidically coupled to the flow cell when the valve is in a second state and fluidically decoupled from the flow cell when the valve is in a first state is provided.

In certain embodiments, the pressure device comprises a pressure chamber fluidically coupled to the flow cell when the valve is in the second state and fluidically decoupled from the cell when the valve is in the first state. In other embodiments, the pressure device further comprises a pump configured to provide a negative pressure in the pressure chamber. In additional embodiments, the system can include a processor electrically coupled to the valve and the sensor and configured to switch the state of the valve between the first state and the second state. In some instances, the processor can be configured to switch the valve from the first state to the second state if the sensor detects a reference time that exceeds a threshold value. In other embodiments, the processor can be configured to maintain the valve in the first state if the reference time is below a threshold value. In certain embodiments, the system can include a detector configured to detect sample in the flow cell. In other embodiments, the system can include a reservoir comprising a cleaning fluid, in which the reservoir is fluidically coupled to the flow cell. In further embodiments, the system can include a fluid flow line between the sample introduction device and the flow cell, in which the fluid flow line is sized and arranged to provide a reference sample from the sample introduction device to the flow cell at a selected or given reference time. In certain examples, the valve is configured as a 3-way solenoid valve.

In another aspect, a system comprising a flow cell fluidically coupled to a valve and a pressure device when the valve is in a second state, in which the flow cell is fluidically decoupled from the pressure device when the valve is in a first state, the pressure device configured to provide a negative pressure when the valve is in the second state to accelerate flow of sample into the flow cell is described.

In certain embodiments, the pressure device comprises a pressure chamber fluidically coupled to the flow cell when the valve is in the second state and fluidically decoupled from the cell when the valve is in the first state. In other embodiments, the pressure device further comprises a pump configured to provide the negative pressure in the pressure chamber. In some examples, the system comprises a processor electrically coupled to the valve and a sensor configured to detect arrival of the sample at a fluid inlet, in which the processor is configured to receive a signal from the sensor and is configured to switch the state of the valve between the first state and the second state. In certain embodiments, the processor can be configured to switch the valve from the first state to the second state if the sensor detects a reference time that exceeds a threshold value. In additional embodiments, the processor can be configured to maintain the valve in the first state if the reference time is below a threshold value. In some examples, the system can include a detector configured to detect sample in the flow cell. In other embodiments, the system can include a reservoir comprising a cleaning fluid, in which the reservoir is fluidically coupled to the flow cell. In further embodiments, the system can include a fluid flow line between the sample introduction device and the flow cell, in which the fluid flow line is sized and arranged to provide a reference sample from the sample introduction device to the flow cell at a selected or given reference time. In some embodiments, the valve is configured as a 3-way solenoid valve.

In an additional aspect, a system comprising a sample introduction device, a flow cell, a fluid flow line between the sample introduction device and the flow cell, in which the fluid flow line is sized and arranged to provide a reference sample from the sample introduction device to the flow cell at a reference time, a sensor, e.g., an ultrasonic sensor, coupled to the fluid inlet of the flow cell and configured to determine the time of arrival of sample at the fluid inlet of the flow cell, a valve, e.g., a 3-way solenoid valve, fluidically coupled to the flow cell and configured to be switched between a first state and a second state, and a pressure device fluidically coupled to the flow cell when the 3-way solenoid valve is in the second state and fluidically decoupled from the flow cell when the 3-way solenoid valve is in the first state, the pressure device comprising a pressure chamber and a pump configured to provide a negative pressure in the pressure chamber to accelerate flow of sample into the flow cell when the 3-way valve is in the second state is provided.

In certain embodiments, the volume of the pressure chamber is at least thirty times greater than the volume of the flow cell. In other embodiments, the fluid flow line is sized and arranged to provide a sample of known viscosity to the flow cell from the sample introduction device at a selected or given reference time. In some examples, the processor can be configured to switch the 3-way valve from the first state to the second state if the ultrasonic sensor detects arrival time of the sample that exceeds the reference time. In certain embodiments, the processor can be configured to maintain the 3-way valve in the first state if the arrival time of the sample is below the threshold time. In additional embodiments, the system can include a detector configured to detect sample in the flow cell. In some examples, the system can include a reservoir comprising a cleaning fluid, in which the reservoir is fluidically coupled to the flow cell. In further examples, the system can be configured to introduce the cleaning fluid into the flow cell to create a turbulent flow to clean the flow cell. In other embodiments, the system can include an additional flow cell fluidically coupled to the sample introduction device, an additional fluid flow line between the sample introduction device and the additional flow cell, in which the additional fluid flow line is sized and arranged to provide a reference sample from the sample introduction device to the additional flow cell at a second reference time, an additional ultrasonic sensor coupled to the fluid inlet of the additional flow cell and configured to determine the time of arrival of sample at the fluid inlet of the additional flow cell, and an additional 3-way solenoid valve fluidically coupled to the flow cell and configured to be switched between a first state and a second state, in which the additional flow cell is fluidically coupled to the pressure device when the additional 3-way solenoid valve is in the second state and fluidically decoupled from the additional flow cell when the additional 3-way solenoid valve is in the first state. In some examples, the sample introduction device can be configured as a manifold with at least two outlets in which a first outlet is fluidically coupled to the flow cell and a second outlet is fluidically coupled to the additional flow cell.

In another aspect, a method of accelerating the flow of sample into a flow cell, the method comprising actuating a valve between a flow cell and a pressure device from a first state to a second state to provide fluidic coupling between the flow cell and the pressure device if a sensed time of sample arrival at the sample cell is greater than a threshold value is provided.

In certain embodiments, the method comprises providing a negative pressure using the pressure device to accelerate the sample into the sample cell. In other embodiments, the method comprises configuring the negative pressure to be about −100 mbar or less, e.g., about −300 mbar. In additional embodiments, the method comprises providing a fluid flow line configured to be placed between a sample introduction device and the flow cell, in which the fluid flow line is sized and arranged to provide a reference sample from the sample introduction device to the flow cell at a selected or given reference time. In further embodiments, the method comprises configuring the fluid flow line to be about 10 inches long. In additional embodiments, the method comprises detecting arrival of sample at the flow cell using an ultrasonic sensor or an optical sensor. In further embodiments, the method comprises detecting sample in the flow cell using an infrared detector. In certain embodiments, the method comprises measuring the time of arrival of the sample at the flow cell and fluidically coupling the flow cell to the pressure device if the arrival time is greater than a threshold time. In some embodiments, the method comprises measuring the time of arrival of the sample at the flow cell and operating the flow cell in a fluidically decoupled state if the arrival time is less than a threshold time. In additional embodiments, the method comprises providing a turbulent flow of a cleaning fluid to the flow cell to remove any residue from the flow cell.

In an additional aspect, a method of accelerating the flow of sample into a flow cell, the method comprising providing a negative pressure from a pressure device fluidically coupled to the flow cell to accelerate filling of the flow cell with the sample is described.

In certain embodiments, the method comprises introducing sample from a sample introduction device into the flow cell fluidically coupled to the sample introduction device, the flow cell comprising a sensor in a fluid inlet, in which the sensor is configured to detect arrival of the sample at the flow cell. In additional embodiments, the method comprises actuating a valve between the pressure device and the sample cell to a position that provides the fluidic coupling between the pressure device and the sample cell if the detected time of sample arrival at the sample cell is greater than a threshold value. In further embodiments, the method comprises configuring the negative pressure to be about −100 mbar or less, e.g., about −200 mbar, −300 mbar or less. In certain examples, the method comprises providing a fluid flow line configured to be placed between a sample introduction device and the flow cell, in which the fluid flow line is sized and arranged to provide a reference sample from the sample introduction device to the flow cell at a selected or given reference time. In certain embodiments, the method comprises detecting arrival of sample at the flow cell using an ultrasonic sensor or an optical sensor. In additional embodiments, the method comprises detecting sample in the flow cell using an infrared detector. In further embodiments, the method comprises measuring the time of arrival of the sample at the flow cell and fluidically coupling the flow cell to the pressure device if the arrival time is greater than a threshold time. In other examples, the method comprises measuring the time of arrival of the sample at the flow cell and operating the flow cell in a fluidically decoupled state if the arrival time is less than a threshold time. In some examples, the method comprises providing a turbulent flow of a cleaning fluid to the flow cell to remove any residue from the flow cell.

In another aspect, a method of loading a flow cell at a selected flow rate where samples of varying viscosity are loaded, the method comprising measuring the arrival time of a sample at an entrance port of the flow cell, and fluidically coupling the flow cell to a pressure device providing a negative pressure to accelerate filling of the flow cell to the selected flow rate if the measured arrival time exceeds a threshold value is described.

In certain embodiments, the method comprises measuring the arrival time of the sample using an ultrasonic sensor or other suitable sensor, e.g., an optical sensor. In some examples, the method comprises actuating a 3-way solenoid valve to a second state to provide the fluidic coupling between the flow cell and the pressure device. In further embodiments, the method comprises adjusting the negative pressure to be about −100 mbar or less. In some embodiments, the method comprises providing a fluid flow line configured to be placed between a sample introduction device and the flow cell, in which the fluid flow line is sized and arranged to provide a reference sample from the sample introduction device to the flow cell at a selected or given reference time. In additional embodiments, the method comprises providing the negative pressure from a pressure device comprising a pressure chamber with a volume at least thirty times larger than the volume of the flow cell. In certain embodiments, the method comprises providing a selected negative pressure to the flow cell during filling of the flow cell. In further examples, the method comprises introducing a turbulent flow of a cleaning fluid into the flow cell to remove any residual sample from the flow cell. In some embodiments, the method comprises configuring the negative pressure to be less than or equal to −500 mbar during introduction of the cleaning fluid.

In further embodiments, a kit comprising a flow cell comprising a first port configured to provide fluidic coupling between the flow cell and a sample introduction device, and a fluid flow line configured to be coupled to the first port of the flow cell and sized and arranged to be placed between the flow cell and the sample introduction device to provide a sample of known viscosity to the flow cell from the sample introduction device at a selected time is provided.

In some examples, the kit comprises a sensor configured to be coupled to the first port of the flow cell to detect arrival of the sample at the flow cell. In certain embodiments, the kit sensor is an ultrasonic sensor or other suitable sensor. In some examples, the kit comprises a detector configured to detect species in the flow cell. In some embodiments, the kit comprises a second fluid flow line configured to be coupled to the first port of the flow cell and sized and arranged to be placed between the flow cell and the sample introduction device to provide a sample of known viscosity to the flow cell from the sample introduction device at a selected time different from the selected time provided by the fluid flow line. In further embodiments, the kit comprises a valve configured to provide fluidic coupling between the flow cell and a pressure device in a second state of the valve and configured to provide fluidic decoupling between the flow cell and the pressure device in a first state of the valve. In additional embodiments, the kit comprises a pressure device configured to provide a negative pressure in the flow cell when the valve is in the second state. In other examples, the pressure device of the kit comprises a pump configured to provide a negative pressure in a pressure chamber of the pressure device. In some embodiments, the valve of the kit is configured as a 3-way solenoid valve. In other embodiments, the kit comprises a reservoir comprising a cleaning fluid.

In other embodiments, a downhole tool for measuring samples of varying viscosity during a drilling operation is provided. In certain examples, the downhole tool comprises a flow cell comprising a fluid inlet, a sensor coupled to the fluid inlet of the flow cell and configured to determine the time of arrival of sample at the fluid inlet of the flow cell, a valve fluidically coupled to the flow cell, and a pressure device fluidically coupled to the flow cell when the valve is in a second state and fluidically decoupled from the flow cell when the valve is in a first state, the pressure device configured to provide a negative pressure to the flow cell when the valve is in the second state.

In certain examples, the flow cell of the downhole tool is fluidically coupled to a fluid flow line between a sample introduction device and the flow cell, in which the fluid flow line is sized and arranged to provide a reference sample from the sample introduction device to the flow cell at a reference time. In other examples, the downhole tool is configured to actuate the valve from the first state to the second state if arrival of the sample at the fluid inlet is greater than the threshold arrival time. In some embodiments, the downhole tool comprises a sensor, e.g., an ultrasonic sensor, configured to detect arrival of the sample at the fluid inlet. In certain examples, the downhole tool comprises a detector configured to detect sample in the flow cell. In additional examples, the detector of the downhole is configured as an optical detector, e.g., an FTIR. In some embodiments, the pressure device of the downhole tool is configured to provide a negative pressure of about −100 mbar or less, e.g., about −300 mbar or less. In other examples, the downhole tool can include a reservoir comprising a cleaning fluid, in which the reservoir is fluidically coupled to the flow cell. In certain embodiments, the pressure device of the downhole tool is configured to provide a negative pressure less than or equal to −500 mbar during introduction of the cleaning fluid to provide a turbulent flow of cleaning fluid to the flow cell.

In another aspect, a method of filling a flow cell to provide a desired filling time is provided. In certain embodiments, the method comprises filling the flow cell at a fill time T using Equation [2]

$$T=(C_1+kx-C_2x^2+C_3P+C_4xP)\times z+x \quad [2]$$

where $C_1$, $C_2$, $C_3$ and $C_4$ are constants determined empirically from a graph of fill times versus reference times, k is a constant, x is a reference time, P is a pre-pump pressure in mbar before a dispense operation is initiated and z is a Fill Factor.

In certain embodiments, the fill factor comprises a scaling factor that controls how far the fill extends beyond the top of an optical window of the flow cell. In other embodiments, the method comprises using a timing line comprising a length of about 10 inches, an outer diameter of about $\frac{1}{8}^{th}$ of an inch and an inner diameter of about $\frac{2}{16}^{th}$ of an inch. In additional embodiments, $C_1$ is 1423, $C_2$ is $2.882\times 10^{-5}$, $C_3$ is 2.143, $C_4$ is $2.491\times 10^{-3}$, k is 2.0 or 2.2, and z is 1.3. In some examples, the method can include adjusting the pressure P to be an effective pressure to provide a selected fill time for the flow cell for a selected sample. In further examples, the method can include adjusting the pressure P to an effective pressure to provide a turbulent flow of a cleaning fluid into the flow cell. In additional examples, the method can include using Equation [2] to fill the flow cell if the reference time exceeds a threshold value. In further embodiments, the method can include passively filling the flow cell if the reference time is less than a threshold value. In some embodiments, the method can include analyzing a plurality of samples, in which the fill time for each sample is selected using equation [2].

Additional features, aspects and examples are described in more detail below.

BRIEF DESCRIPTION OF THE FIGURES

Certain illustrative embodiments are described in more detail below with reference to the accompanying figures in which:

FIG. 8 is a table showing measured filling times with various fluids of different viscosities, in accordance with certain examples.

Figure 2:
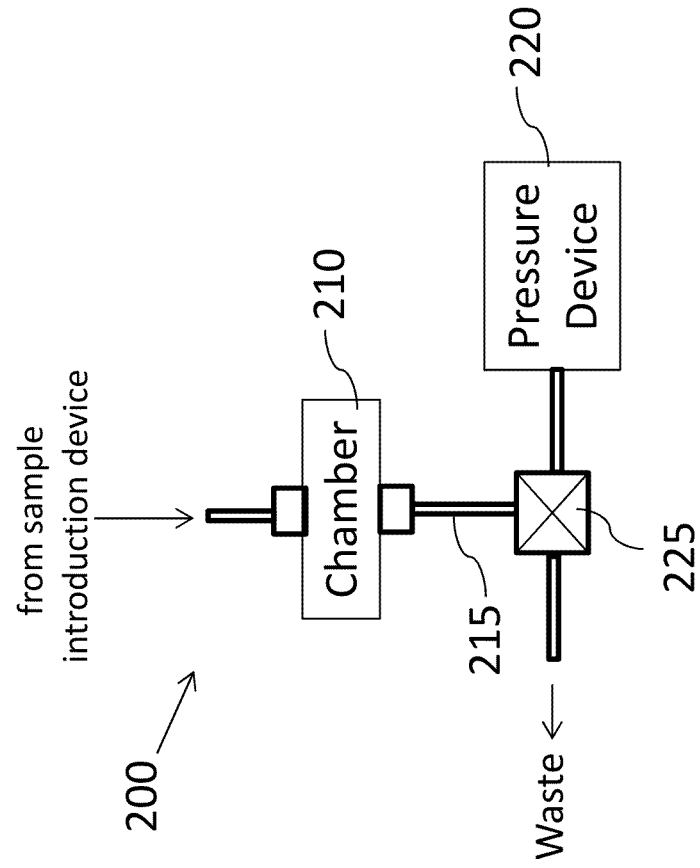
FIG. 2 is an illustration of a system configured for use in an vacuum assisted filling or active mode, in accordance with certain examples.

It will be recognized by the person of ordinary skill in the art, given the benefit of this disclosure, that the relative positions and sizes of the components in the figures are not limiting and that no particular size, dimension, thickness or arrangement is implied as being required based on the representations of the components shown in the figures.

DETAILED DESCRIPTION

Certain specific examples are described below to illustrate further some of the novel aspects of the technology described herein. The term fluid as used herein is intended to refer to gases and liquids and other states of matter that can flow. In some embodiments, the term fluid is used to describe viscous samples that may flow slower than desired through a selected fluid line.

In certain embodiments, many high-throughput screening and monitoring applications require the repeated delivery of samples into a flow cell where a measurement (optical or otherwise) is performed. After measurement, the sample is flushed and the cell washed with solvent in preparation for the next sample. Where the samples under test all share similar viscosity values, a simple delivery system (e.g. from a pipette driven by a motor driven syringe) can be configured to provide a reliable filling process for all samples, although the filling time may be slow if the samples being analyzed have moderate to high viscosity. In situations where sample viscosities vary widely, a conventional filling system would typically have to be configured for worst case sample conditions (i.e. highest viscosities) leading to low overall throughput rates.

Certain embodiments described herein provide a rapid and efficient solution to filling a flow cell where the samples to be measured span a wide range of viscosities. Desirable attributes provided by certain embodiments include, for example, the filling time can be automatically determined on a per-sample basis, with the result that throughput rates are not limited by worst-case sample conditions; a mechanism can be employed to accelerate the movement of fluid into the flow cell, enabling significantly faster average fill times than is possible with a conventional filling system, the ability to switch on the sample filling acceleration mechanism adaptively when required according to sample viscosity; the volume of cleaning solvent can be automatically calculated on a per-sample basis; in addition, the cleaning process can be highly turbulent and consequently very efficient. These attributes enable minimization of cleaning times and solvent volumes.

In certain examples, the systems described herein can include a fluid circuit configuration to enable a flow cell to be rapidly filled with sample. The fluid circuit can include many different components depending on the desired configuration, and illustrative components include, but are not limited to, a fill cup assembly at which sample can be delivered from a syringe based pipette system, e.g., an autosampler deck. If desired, the pipette can form a seal with the fill cup during sample injection. In some examples, the system can include a sensor, positioned at the inlet of the flow cell, that is configured to detect arrival of the sample. In certain examples, the system can include a pressure chamber positioned downstream of the flow cell to provide a known negative pressure prior to the delivery of sample into the system. In some embodiments, a valve may be positioned between the flow cell and the pressure chamber to enable the pressure upstream of the sample to be switched between atmospheric pressure and a negative pressure of the pressure chamber. The system can be used, for example, as follows: after the sample is injected, the time taken to trigger the sample sensor is measured. The timing measurement can be used to determine whether to use active or passive filling of the cell. If the passive or direct filling is selected, sample is permitted to flow into the sample cell propelled by the back pressure in the pipette tip. If the active or assisted filling is selected, the negative pressure can be used to accelerate flow of sample into the sample flow cell. After measurement and/or evacuation of the sample from the flow cell, the calculated volume of solvent can be introduced into the fill cup in a series of shots or injections. The pressure chamber can be continuously pumped to draw solvent through the cell with high speed and turbulence to achieve efficient washing of the cell.

In certain embodiments, the systems, methods and devices described herein can be used in many different applications including, but not limited to, food sampling, blood screening, water quality monitoring, oil/gas monitoring and measurements and in other applications where different fluid samples may have different viscosities. If desired, the fluids may be separated prior to introduction into a cell, e.g., using chromatography, such that fluid comprising only one or a few species is measured at any one time.

In certain embodiments, the devices, systems and methods described herein can include one or more fluid flow lines sized and arranged to provide a reference sample to a flow cell at a selected, determined or given reference time. For example, a fluid flow line can be sized such that a fluid of known viscosity can be provided from a sample introduction device, e.g., a pipette, autosampler, etc. In certain instances herein, such fluid flow line may be referred to as a "timing line." In some examples, the timing line can be used to determine if a sample is provided to a flow cell within a desired time. For example, if a sample is provided to a flow cell at a time larger than a threshold time, then it may be desirable to increase the flow rate of the sample into the flow cell, e.g., by providing a negative pressure to accelerate sample flow into the flow cell. Where the sample is provided to a flow cell at a time less than a threshold time, the sample flow rate may continue to flow without any negative pressure assistance. In certain embodiments, the devices, methods and systems described herein can desirably use active flow to accelerate the flow of viscous fluid samples into a chamber, also referred to in certain instances as a flow cell or sample cell or sample chamber. In certain examples, the active flow may be provided through fluidic coupling of the chamber with a pressure device such as, for example, a pump, a pressure chamber or a combination thereof. In some embodiments, the pressure device can be configured to provide a negative pressure relative to atmospheric pressure such that fluid sample is drawn more rapidly into the chamber when compared to the fill rate using passive flow, e.g., using flow through a system open to atmospheric pressure at a fluid outlet or at zero gauge pressure.

Figure 1:
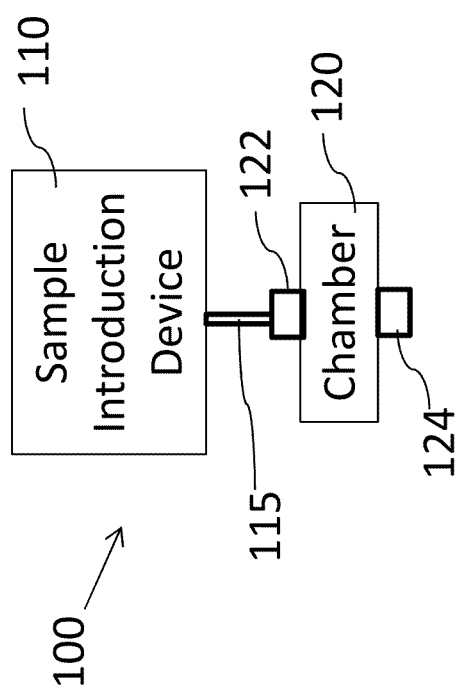
FIG. 1 is an illustration of a system configured for use in a direct filling or passive mode, in accordance with certain examples.

In certain examples where passive flow, also referred to in certain instances as direct flow, is implemented pneumatic pressure from a sample introduction device can be used to introduce a sample into a chamber. For example and referring to FIG. 1, a system 100 can include a sample introduction device 110 fluidically coupled to a sample chamber 120, which is generally designed to receive sample and/or retain sample for analysis. The sample chamber 120 can include a fluid inlet 122 fluidically coupled to the sample introduction device 110 through a timing line 115 and a fluid outlet 124 which may flow to waste, a trap or other suitable systems or devices. While the fluid inlet 122 and outlet 124 are shown as separate components from the sample chamber 120 for ease of description, the sample chamber 120 typically includes an integral fluid inlet and an integral fluid outlet. In some embodiments, the fluid outlet 124 may be exposed to the atmosphere such that pneumatic pressure from the sample introduction device 110 results in flow of sample from the sample introduction device 110 into the sample chamber 120 and to waste through the fluid outlet 124. For example, a sample introduction device 110 can be configured to provide positive pressure to force sample from the sample introduction device 110 into the sample chamber 120. Illustrations of suitable sample introduction devices are described in more detail below.

In certain embodiments, the timing line 115 can be sized and arranged such that a reference sample, e.g., one of known viscosity, is provided from the sample introduction device 110 to the sample chamber 120 at a selected or given reference time. In some embodiments, the dimensions of the timing line 115 are selected such that the reference sample is provided from the sample introduction device 110 to the sample chamber 120 within a selected threshold time, e.g., 500 milliseconds or less. This threshold time or value can be used to compare the arrival time of unknown samples at the sample chamber 120. For example, a sensor (not shown) can be present in the sample chamber 120, the fluid inlet 122 or both, in which the sensor is configured to detect the presence of sample. The exact nature of the sensor can vary depending on the sample properties and illustrative sensors are described in more detail below. In some embodiments, the time from sample introduction to sensing of sample arrival by the sensor can be compared to the threshold time. If the arrival time of the sample is less than the threshold time, then the system may operate using the passive filling, e.g., at atmospheric pressure on the downstream side of the sample chamber 120. For example, passive filling may be suitable for use with samples of low viscosity that can flow quickly from the sample introduction device 110 to the chamber sample 120. If the arrival time of the sample is greater than the threshold time, then active filling can be implemented to reduce sample arrival time. For example, where a highly viscous sample is loaded from the sample introduction device, the viscous sample may flow slowly through the timing line 115 and arrive at the sample chamber 120 at a time that exceeds the threshold time. In some embodiments, the level or degree of active filling implemented can be selected such that actual sample arrival time is selected to be a desired arrival time. For example, the pressure provided by a pressure device can be selected such that sample flow is accelerated to an effective amount to provide a selected sample arrival time.

In some embodiments, the arrival time of the sample can vary based on the physical properties of the sample including but not limited to viscosity, polarity, component make-up or other physical properties of the sample. For example, the sample arrival time at the sample chamber 120 may vary with the viscosity of the fluid, e.g., certain liquids may be more viscous and generally take longer to flow into the sample chamber 120. To increase the flow rate into the chamber, or to decrease the filling time of sample in the sample chamber 120, the sample chamber 120 may be fluidically coupled to a pressure device configured to accelerate sample flow into the sample chamber 120 at least under certain conditions. One schematic of a system including a pressure device is shown in FIG. 2. The system 200 includes a sample chamber 210 configured to be fluidically coupled to a pressure device 220. In some examples, a valve 225, e.g., a 3-way solenoid valve, can be positioned in a fluid line 215 between the sample chamber 210 and the pressure device 220. When the system 200 is operating in the passive or direct mode, the valve 220 can be configured to permit fluidic coupling between the atmosphere and the sample chamber 210 such that fluid generally flows from the sample introduction device (not shown) into the sample chamber 210 and out to waste once sample measurements have been performed. In the passive configuration, the pressure device 220 is fluidically decoupled to the sample chamber 210, e.g., the valve is in a first position or state to prevent fluid flow or fluidic coupling between the sample chamber 210 and the pressure device 220. Where viscous samples are being used, it can be desirable to actuate the valve 220 to a second position where the pressure device 220 becomes fluidically coupled to the sample chamber 210 to accelerate flow of sample into the sample chamber 210 and decrease the overall filling time of the sample chamber 210. When the pressure device 220 is fluidically coupled to the sample chamber 210, active or assisted flow can be used to accelerate the flow of sample into the sample chamber 210. In certain embodiments, the pressure device 220 can be configured with, or configured to provide, a pressure less than atmospheric pressure such that sample flow from the sample introduction device (not shown) is accelerated into the sample chamber 210 to reduce overall filling time. Such a negative pressure can result in an increased pressure differential between the sample introduction device and the sample chamber 210 such that sample flow into the sample chamber 210 is accelerated. In some embodiments, the negative pressure may be less than −100 mbar, e.g., −200 mbar, −300 mbar or −400 mbar.

In embodiments where active or assisted flow is used, the pressure device 220 may provide at a generally constant pressure or may be configured to provide a pressure that can vary depending on the nature of the sample. For example, it may be desirable to set the pressure of the pressure device 220 at a fixed negative pressure that can be used with many different types of samples. In other configurations, the pressure provided by the pressure device 220 may vary, e.g., a more negative pressure can be used where highly viscous samples are used compared to the pressure used with less viscous samples. In some embodiments, the provided pressure may be pulsed or provided in incremental bursts to accelerate sample into the sample chamber 210. Such pulsing or bursts may occur by actuating the valve 225 between the different states at a desired frequency. In some instances, the valve can be actuated at an effective frequency such that sample flow from sample introduction device to the sample chamber 210 appears to flow continuously. By pulsing the valve at an effective frequency, incremental periods of active and passive flow may be implemented to better assist in controlling sample flow into the sample chamber 210.

In certain embodiments, once the sample chamber 210 has been filled with sample, the valve 225 may be actuated to a position where the sample chamber 210 becomes fluidically decoupled from the pressure device 220. Measurement of the sample in the sample chamber 210 may then take place using one or more suitable techniques as described herein. In some embodiments, all flow of sample into the sample chamber 220 may be stopped during measurement, whereas in other examples flow of sample through the flow cell may continue during measurement of the sample in the chamber 220.

In certain configurations, the pressure device 220 can include one or more pumps, e.g., a vacuum pump, configured to provide a negative pressure relative to atmospheric pressure. In some embodiments, the pump may be coupled directly to the chamber without any intervening components, whereas in other embodiments, the pump may be coupled to a pressure chamber that is positioned between the sample chamber and the pump. In embodiments where a pressure chamber is present, the volume of the pressure chamber may be substantially larger than the volume of the sample chamber such that a rapid pressure drop to a desired negative pressure can be achieved when the pressure chamber and the sample chamber are fluidically coupled. In certain embodiments, the volume of the pressure chamber may be about five times, ten times, twenty times, fifty times or 100 times larger than the volume of the flow cell. For example, the flow cell may have a volume of about 100-200 microliters, and the pressure chamber may have a volume of about 100-200 milliliters. In some embodiments, the sample may flow into the sample chamber where it can be analyzed and then may flow into the pressure chamber and onto waste. In other embodiments, the sample flow may flow into the sample chamber where it can be analyzed and then may flow directly out of the system and to waste or a trap without passing through the pressure chamber itself. In some embodiments, the pressure chamber can function as a trap with sample and any wash or cleaning fluid used flowing into the pressure chamber. The pressure chamber may subsequently be emptied by opening a valve, applying a positive pressure using a pump or by other means.

In certain embodiments, a sensor can be present in the fluid inlet of the chamber to sense or otherwise determine directly or indirectly the viscosity of the sample. Sample viscosity may be determined indirectly by measuring the time it takes a sample to travel from an injection point to the sensor, e.g., the time it take the sample to travel through the timing line and arrive at the sample chamber. In some embodiments, the sensor can be used to detect the arrival of sample at the sample chamber. The arrival time of the sample can be used to determine whether or not passive or active flow should be used. For example, the time it takes to trigger the sensor, e.g., the sensor is triggered as soon as the sample arrives at the chamber, can be compared to a threshold value, and if the trigger time is greater than the threshold value, active flow can be implemented to accelerate sample into the chamber. If the trigger time is less than the threshold value, then passive flow may continue to be used, e.g., positive air pressure provided by the sample introduction device can be used to provide flow of sample into the flow cell. In certain embodiments, the sensor may be an ultrasonic sensor configured to detect the presence of sample at the fluid inlet of the flow cell. The ultrasonic sensor is generally insensitive to color or discoloration of the sample or tubing and may be desirable to use where sooty or dark samples are present that might interfere with optical sensors. In other embodiments, an optical sensor can be used that is configured to detect a difference in light transmitted when the sample is present versus the sample not being present. In additional embodiments, a magnetic sensor can be used to detect when a sample comprising magnetic species arrives at the chamber. Notwithstanding that many different types of sensors can be used to detect sample arrival, the sensor is generally configured to provide a reference state or condition prior to any sample being introduced. This condition can be continuously monitored or polled intervally, and when a change in the condition is noted, e.g., when sample is present, this time can be recorded. For example, a timing period can be initiated when sample is introduced from the sample introduction device. When sample is sensed by the sensor, the timing period can be stopped and the sample arrival time $t_{sensor}$ is the total time between the beginning of sample introduction and sample sensing by the sensor.

In some embodiments described herein, a simple comparison step between $t_{sensor}$ and a threshold time ($t_{thresh}$) can be performed to determine if active or passive filling should be selected. Where $t_{thresh}$ is greater than $t_{sensor}$, passive filling may be performed. Where $t_{sensor}$ is greater than or equal to $t_{thresh}$, then active filling may be implemented to accelerate sample flow into the flow cell. Such a comparison can be performed on an injection by injection basis to determine whether or not to use passive or active filling during operation of the system.

In other embodiments, rather than use a simple comparison step, an algorithm can be implemented to determine whether active or passive filling should be used and the level of pressure that is used to provide a desired fill rate. For example, the time at which sample introduction is complete can be recorded as $t_{injection}$. The sensor can be continuously polled to determine when sample arrives at the flow cell. This time can be recorded as $t_{sensor}$. If the sensor is triggered prior to introduction of all sample from the sample introduction device, then a reference time for sample arrival would be $t_{reference} = t_{sensor} - t_{injection}$, which would provide a negative value as the sample will have arrived prior to completion of injection. If the injection completes prior to any sample arriving at the flow cell, then the calculated $t_{reference}$ value would be positive as $t_{sensor}$ would be greater than $t_{injection}$.

In certain embodiments, the calculated reference time ($t_{reference}$ or $t_{ref}$) can be compared to a threshold time ($t_{thresh}$), which is based on the dimensions and size of the timing line and the time it takes for a sample of known viscosity to arrive at the flow cell. Several scenarios exist when $t_{reference}$ is compared to $t_{thresh}$ including where $t_{reference} < t_{thresh}$, then use passive filling, or where $t_{reference} \geq t_{thresh}$, then use active filling. In certain embodiments, the desired fill time $t_{fill}$ can be computed from the functional relationship between $t_{reference}$ and $t_{fill}$. In one configuration, a linear relationship can be used to provide an algorithm suitable for determining the fill time ($t_{fill}$) as shown in Equation [1] below.

$$T = A_1 \times x + A_2 \quad [1]$$

Where $A_1$ and $A_2$ are constants, T is the fill time and x is $t_{ref}$. In an alternative configuration, a more complex algorithm can be used to determine the fill time ($t_{fill}$) as shown in Equation [2] below. The more complex algorithm may provide for better and/or finer adjustment of the filling time. In general the fill time $t_{fill}$ or T is a function of the reference time $t_{ref}$, the pre-pump pressure in millibar measured just before the dispense operation starts and the position k of the flow cell in the spectrometer (lower or upper position). Mathematically, the relationship may be represented as $$T = (C_1 + kx - C_2 x^2 + C_3 P + C_4 xP) \times z + x \quad [2]$$

where T is the fill time, $C_1$, $C_2$, $C_3$ and $C_4$ are constants, x is the reference time $t_{ref}$, P is the pre-pump pressure in millibar measured just before the dispense operation starts and z is the Fill Factor, which is a scaling factor that controls how far the fill extends beyond the top of the optical window of the flow cell. It may be desirable to set a minimum value of 500 milliseconds for the fill time to trigger filling in the active mode. For example, if the reference time exceeds 500 milliseconds, then the active mode may be implemented.

In some embodiments, the constants $C_1$, $C_2$, $C_3$ and $C_4$ may be determined empirically by performing a series of measurements where the fill time is measured as a function of the reference time. For example, fill time measurements may be taken at a constant pre-pump pressure, e.g., about −200 mBar, about −300 mBar, or about −400 Mbar, and at various reference times to generate a graph of fill times versus reference times. The resulting data may be fitted to the general equation shown in Equation 2 to provide the constants $C_1$, $C_2$, $C_3$ and $C_4$ to provide an algorithm suitable for use in determining if assisted or passive filling is to be implemented for a particular sample.

In some embodiments, a similar algorithm may be used to determine the fill time in the direct or passive filling of the flow cell, as shown in Equation [3]

$$T = C_5 x + C_6 + F \quad [3]$$

where $C_5$ and $C_6$ are constants and F is the fill offset value, which is a timing offset applicable to the direct filing mode. To determine $C_5$ and $C_6$, the offset value may be set at a desired value, e.g., 1000 ms, and measurements may be performed to measure the fill time as a function of the reference time x. These measurements may be graphed and fitted to Equation [3] to provide the value of the constants $C_5$ and $C_6$ for a particular system. The values of the constants will vary with the dimensions of the timing line, and the algorithm for any one particular timing line or a set of timing lines can be determined empirically using Equations [2] and [3].

In certain embodiments, to determine whether the system should use a direct or passive mode or an active or vacuum assisted mode, the value of the reference time may be used. For example, if the value of the reference time is less than a selected threshold value, then the direct or passive mode can be used as the cell is filling in less than the threshold time. If the value of the reference time exceeds or is equal to the selected threshold value, then the active or vacuum assisted mode can be implemented after the sample is loaded into the timing line from the sample introduction system. Once the vacuum assisted mode is implemented, the filling time for the vacuum assisted mode can be determined using Equation [2]. Without wishing to be bound by any particular scientific theory, the fill time ($t_{fill}$) is generally calculated to determine when the filling mode can be switched from active to passive and measurement of the sample may then be performed. For example, once the fill time ($t_{fill}$) has elapsed, the flow cell should be filled with sample and the valve of the system can be switched to fluidically decouple the flow cell from the pressure chamber and generally halt flow of sample into the flow cell. Where direct or passive filling is used, the sample introduction device may remain engaged to avoid creating a back pressure that might disturb the sample during measurement. Where active or vacuum filling is used, the sample introduction device may be removed during measurement of the sample in the flow cell.

In certain embodiments, once measurement of the sample has taken place, it may be desirable to flush the flow cell to remove any sample within the flow cell such that subsequent measurements are not contaminated by any residue from a prior sample. Due to the highly viscous nature of certain samples, simple flushing with a fluid may not be sufficient to remove the sample from the flow cell, e.g., viscous sample may remain on the surfaces of the flow cell and contaminate any subsequently introduced sample. To provide increased washing of the flow cell and enhanced removal of any sample from the flow cell, the active filling mode can be implemented in combination with one or more wash fluids. For example and referring to FIG. 2 again, the valve 225 can be switched to provide fluidic coupling between the pressure device 220 and the sample chamber 210, which will act to draw sample out of the chamber 220 through the fluid line 215. A continuous or intermittent stream of a cleaning fluid can be provided by a sample introduction device or another fluid device that can introduce sample into the sample chamber 210. Injecting intermittent bursts of cleaning fluid into the sample chamber 210 in combination with pressure from the pressure device 220 can cause turbulent flow or cavitation of the cleaning fluid through the sample chamber 210, which acts to remove residual sample from the sample chamber 210. Additional air may be drawn in with the cleaning fluid to enhance the turbulent flow in the sample chamber 210 and/or dry the sample chamber 210 prior to subsequent introduction of another sample. The volume of cleaning fluid used may be calculated from the reference time $t_{ref}$ according to Equations [4] and [5].

$$W=\text{Floor}[C_7+S_{max}+(S_{min}-S_{max})\exp(-C8 \times x)] \text{ if } t_{ref}>0 \quad [4]$$

$$W=S_{min} \text{ if } t_{ref} \leq 0 \quad [5]$$

where W is the number of aliquots of a selected volume, e.g., 500 microliters, used to wash the flow cell, $S_{max}$ is a maximum number of aliquots, $S_{min}$ is a minimum number of aliquots, $C_7$ and $C_8$ are constants. The Floor function Floor (N) provides the largest integer not greater than N. The number of washes cannot exceed $S_{max}$ or drop below $S_{min}$. In some instances, about 1.2, 1.5 or 2 times the amount of calculated cleaning fluid can be used to ensure any residual sample has been removed from the sample chamber 210. In some embodiments where passive filling is used, a minimal number of washes can be used as the sample is likely to be less viscous than samples used with active filling. For example, the system can be configured such that a minimum number of washes, e.g., 4-5 wash injections, are used where passive filling has been used to fill the flow cell. Where active filling has been used to fill the flow cell, the number of washes generally correlates to the viscosity of the sample with more viscous samples desirably including more wash injections. In some configurations, the system can be configured such that a maximum number of wash injections is selected, e.g., 15-20 separate wash injections, where the $t_{reference}$ values are substantially larger than the $t_{thresh}$ values, e.g., where $t_{ref}$ values are 2×, 3×, 4×, 5× or more larger than $t_{thresh}$. In certain embodiments, subsequent to injection of the cleaning fluid, the active filling condition can be maintained for an effective period to dry the sample chamber 210. In particular, air can be drawn in through the sample chamber 210 and exits into the pressure device 220 to enhance drying of the sample chamber 210 and removal of any residual cleaning fluid in the sample chamber 210. In certain embodiments, the pressure used during the washing steps may be about −400 mbar or less, e.g., −500 mbar or −600 mbar.

Figure 3:
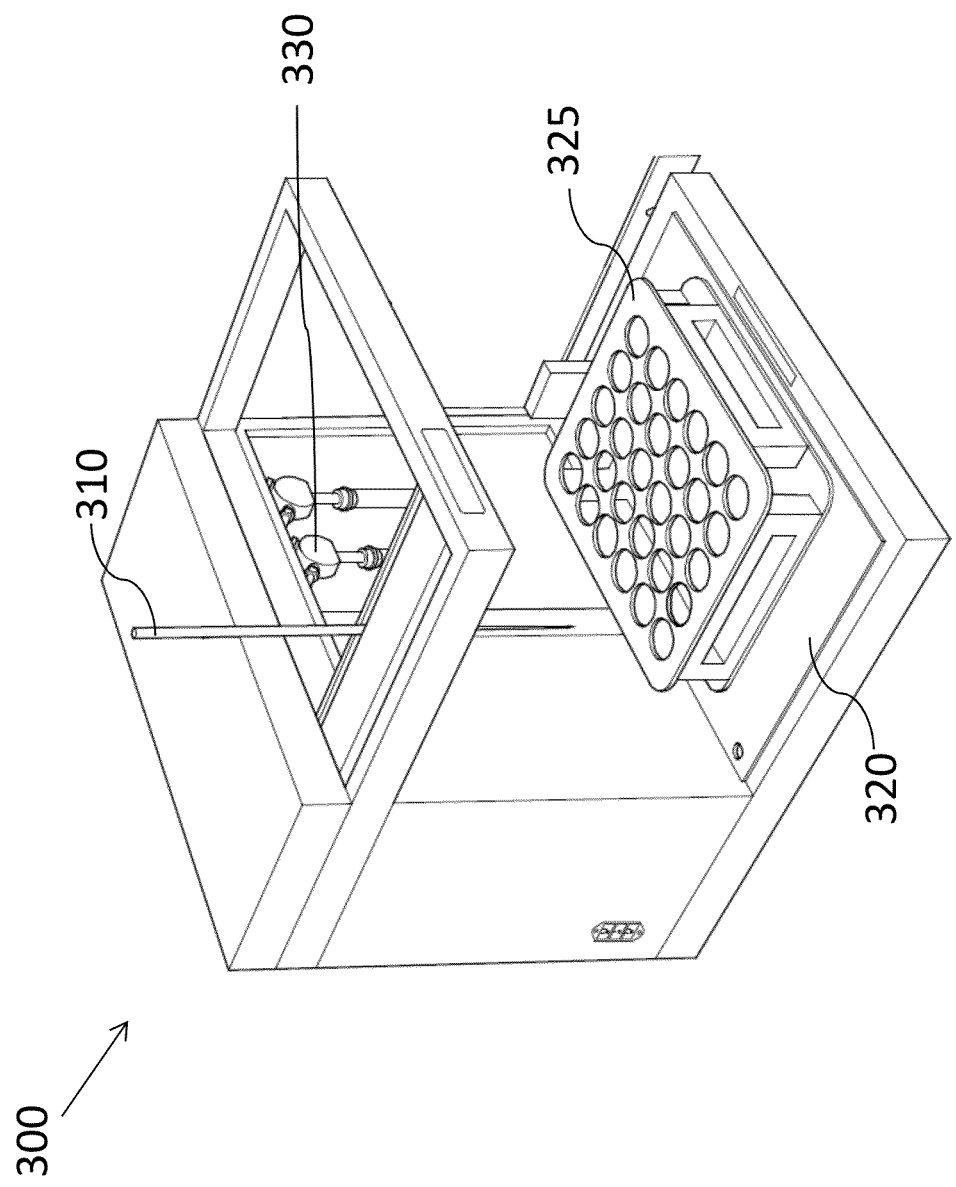
FIG. 3 is an illustration of a sample introduction system, in accordance with certain examples.

In certain embodiments, an illustration of a sample introduction device suitable for use with the systems described herein is shown in FIG. 3. The sample introduction device 300 comprises at least one syringe 310 that can be used to load sample into the body of the syringe 310 and subsequently load sample into a fill cup (not shown) or sampling assembly from the syringe. The syringe 310 typically includes a needle that can engage to the fill cup and load the sample into the fill cup. The fill cup is fluidically coupled to the flow cell to provide sample from the fill cup, through the timing line and to the flow cell at a selected fill time or rate. The sample introduction device 300 also includes a deck or surface 320 that can receive a device holding one or more samples such as, for example, the rack 325 shown in FIG. 3. In operation, a device including a plurality of samples may be placed on the surface or deck 320. The syringe can be lowered into one of the tubes in the rack to extract sample from the tube. Extraction typically occurs by engaging a pump 330 fluidically coupled to the syringe to draw sample into the needle of the syringe through pressure provided by the pump. A transfer port such as, for example, a fill cup can be used to deliver sample from the syringe to the flow cell if desired. After measurement of sample, the syringe may be washed by moving the syringe to a wash port where cleaning fluid or solvent can be introduced into the syringe. Cleaning fluid may introduced into the needle and the sample cell using vacuum filling as described herein or can be introduced using passive filling.

In certain embodiments, in a typical sampling procedure the needle is lowered into the sample and sample is drawn into the needle by drawing down of the sample pump. This provides for introduction of sample into the needle with an air head or column above the sample. The needle with sample may then be moved to a transfer port or fill cup, where it can be lowered and engage the transfer port. In passive filling of the flow cell, the needle typically remains engaged to the transfer port during measurement of the sample, whereas in active or assisted filling of the flow cell, the needle is typically removed from the transfer port during measurement though it may remain engaged if desired. After measurement of the sample, the needle may be moved to a waste port to dispense any remaining sample, and the needle can be washed as described herein, e.g., using cleaning fluid and assisted filling to cause turbulent flow of the cleaning fluid and enhance cleaning of the flow cell. Once the needle and flow cell have been cleaned, a new sample may be introduced into the sample introduction device and flow cell for analysis. If desired, the flow cell may include more than a single port to receive sample from two different fill cup assemblies or transfer ports. In some embodiments, the spectrometer may include an upper position and a lower position for measurement of sample in the flow cell.

In certain embodiments, the systems described herein can be configured such that a selected fill rate, or if desired a substantially constant filling time, is implemented notwithstanding that different samples may have different viscosities. For example, the system can be configured such that the flow cell fill time is between about 250 milliseconds to about 30 seconds, more particularly about 500 milliseconds to about 25 seconds, e.g., about 5 seconds to about 20 seconds, or any value between these illustrative ranges. To provide a faster filling time, larger pressure differentials can be implemented to increase flow of viscous samples into the flow cell. Where less viscous samples are present, the pressure differential can be reduced or the system can be operated in a passive mode.

In certain embodiments, the systems described herein can include more than one flow cell. For example, the system can include an additional flow cell fluidically coupled to the sample introduction device. The sample introduction device may take the form of a manifold or other suitable device that can provide sample to more than a single flow cell. In some examples, the system can include an additional fluid flow line between the sample introduction device and the additional flow cell, in which the additional fluid flow line is sized and arranged to provide a reference sample from the sample introduction device to the additional flow cell at a second reference time. If desired, an additional sensor, e.g., an ultrasonic sensor can be coupled to the fluid inlet of the additional flow cell and configured to determine the time of arrival of sample at the fluid inlet of the additional flow cell. In some embodiments, a single sensor can be used with two or more flow cells. In certain embodiments, the system can include an additional 3-way solenoid valve fluidically coupled to the additional flow cell and configured to be switched between a first state and a second state, in which the additional flow cell is fluidically coupled to the pressure device when the additional 3-way solenoid valve is in the second state and fluidically decoupled from the additional flow cell when the additional 3-way solenoid valve is in the first state. If desired, each flow cell can be fluidically coupled to its own pressure device or a single pressure device can be used for two or more flow cells. In some examples, the sample introduction device can be configured as a manifold with at least two outlets in which a first outlet is fluidically coupled to the flow cell and a second outlet is fluidically coupled to the additional flow cell.

Figure 4:
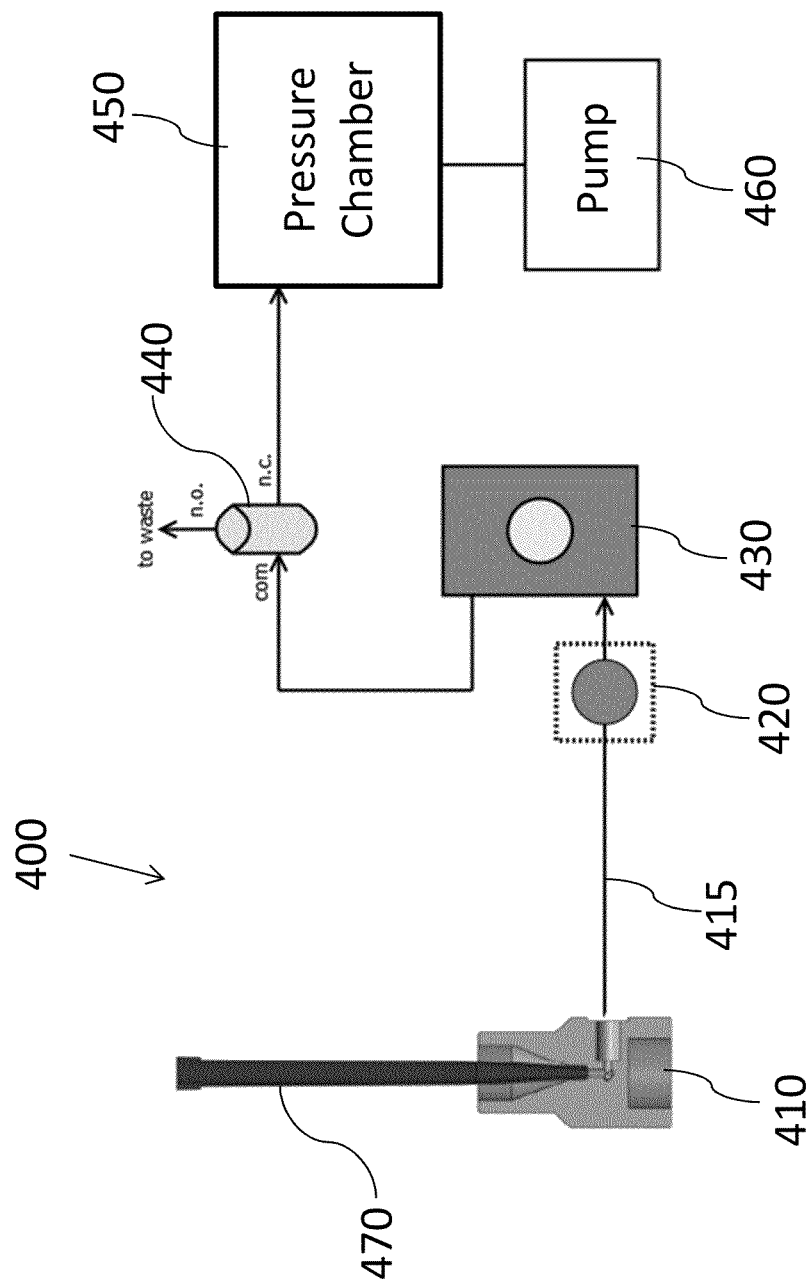
FIG. 4 is an illustration of a system comprising a flow cell, a valve and a pressure chamber, in accordance with certain examples.

An illustrative configuration of a system that can be used to provide direct and active filling is shown in FIG. 4. The components of the system 400 include a fill cup assembly 410 that is configured to receive a sample from a syringe based pipette system (e.g., an autosampler system). The tip of the pipette tip 470 forms a seal with the fill cup 410 during sample injection. An air gap exists in the pipette tip separating the system (syringe) fluid from the sample fluid. This air column is compressed when the syringe actuates, and the compressed air then drives sample into the fill cup 410. A fluid line 415 with a defined length and bore, i.e., a timing line, fluidically couples the fill cup 410 to a flow cell 430. In certain embodiments, the fluid line 415 may be an inner diameter of about 0.05 inches to about 0.1 inches, e.g., an inner diameter of about $1/16^{th}$ of an inch, and an outer diameter of about 0.1 inches to about 0.2 inches, e.g., an outer diameter of about $1/8^{th}$ of an inch. The overall length of the fluid line 415 can vary from about 2 inches to about 20 inches, e.g., about 5 inches to about 15 inches or about 10 inches. The constants and values used in determining the fill times will vary depending on the particular length and volume of the timing line selected. In some instances, it may be desirable to select the fluid line 415 to be as short as possible while still enabling measurement of the arrival times, reference times and/or fill times and while still permitting samples of different viscosities to have different arrival times, e.g., the fluid line 415 may be selected to be as short as possible without compromising the ability to discriminate between samples of different viscosities.

In certain examples, the flow cell 430 may have an internal volume of about 100-500 microliters, more particularly about 100 to about 300 microliters, for example about 100-150 microliters. In certain instances, the flow cell 430 can include an optically transparent window that can receive a signal, e.g., light, from a detector for measurement of sample. In some embodiments, this optical window or optical region may have a volume of about 10-30 microliters, more particularly about 15-25 microliters, e.g., about 20 microliters. In certain configurations, the path length of the optical region may also vary from about 0.05 mm to about 0.5 mm, for example, about 0.075 mm to about 0.15 mm, e.g., about 0.1 mm. In some embodiments, the diameter of the optical region (when the cross-section is circular) can be from about 10 mm to about 25 mm, more particularly about 15 mm to about 20 mm. The exact cross-sectional shape of the optical region may vary and shapes such as rectangular, square, triangular and other shapes can be used in place of a circular cross-section.

In some embodiments, the combined volume of the fluid line 415 and the flow cell 430 may be about 0.5-3 mL, more particularly about 1-3 mL, 1.5-2.5 mL or 2 mL. A sensor 420 can be positioned the inlet of the flow cell 430 (or in the flow cell 430) to detect the arrival of sample at the flow cell 430. A three way, two position valve 440 can be used to switch the system from the direct or passive filling mode to the active or vacuum assisted filling mode. When the valve 440 is not energized (OFF) the common port (com) is connected to the normally open (n.o.) port, which provides a pressure close to zero gauge pressure or atmospheric pressure in the flow cell 430. When the valve is energized (ON) the common port (com) is connected to the normally closed port (n.c.), which provides a pressure gradient between the flow cell 430 and a pressure chamber 450. The pressure chamber 450 positioned downstream of the valve 440 can be pre-pumped to a known negative gauge pressure, e.g., about −200 mBar to about −500 mBar, prior to the delivery of sample to the fill cup 410. The pressure chamber 410 is used for pressure control and can also be used for the collection of waste sample and solvent, if desired. An upper limit on the chamber volume is generally imposed by space constraints and the need for reasonable pump-down times; however the volume of the chamber can be considerably larger than the volume of the flow circuit to provide substantially constant pressures. In certain embodiments, the pressure chamber may have a volume of about 100 mL to about 200 mL, for example, about 125 mL, 150 mL or 175 mL. In certain embodiments, the volume of the pressure chamber 450 is at least 50× greater than the combined total volume of the flow cell 430 and the fluid line 415, more particularly, the volume of the pressure chamber 450 is at least 60× or 75× greater than the combined total volume of the flow cell 430 and the fluid line 415. The use of constant pressure in the pressure chamber 450 provides precise control of sample movement and provides for the relationship between the reference time ($t_{ref}$) and fill time ($t_{fill}$) as described herein. The pressure chamber is fluidically coupled to a pump 460 which is able to evacuate the pressure chamber and hold this pressure constant (e.g. using an isolation valve) when a target negative gauge pressure is reached. If desired, one or more pressure sensors may be present in the pressure chamber 450 to determine when a desired pressure is reached. In some embodiments, the pump 460 may be configured such that a desired pressure is reached in the pressure chamber from about 1-4 seconds of pumping, e.g., about −300 mbar gauge pressure can be reached after about 2 seconds of pumping. The particular pressure selected for use in the pressure chamber 450 can depend on the sample properties. A more negative pressure can provide for increased fill times but may result in the sample breaking up or bubble formation in the sample in the flow cell 430. Similarly, a less negative pressure reduces the likelihood of sample breakup but increases the overall fill time. As described herein, the pressure may be very negative during the washing step, e.g., less than −500 mbar or −700 mbar or less, to increase turbulent flow and enhanced washing of the flow cell.

In certain embodiments, the systems described herein can be used with samples having a wide range of viscosities. For example, samples with a viscosity up to 1000 cSt (at 40° C.) can be measured with the systems described herein. Systems with viscosities higher than 1000 cSt (at 40° C.) may also be measured by adjusting the fill times and/or pressures used in the pressure chamber. As described herein, samples with low viscosities are generally used with the direct or passive filling mode, and samples with high viscosities are generally used with the active or vacuum assisted mode. While the exact viscosity that is low or high will depend on the particular sample, samples with viscosities above about 20 cSt (at 40° C) are generally considered high viscosity samples.

In certain embodiments, the systems described herein can be used with or can include a detector to detect the sample in the flow cell. Illustrative detectors include ultrasonic detectors, light detectors such as, for example, infrared spectrometers (e.g., FTIR spectrometers), absorbance detectors (e.g., Visible light detectors, Ultraviolet light detectors), emission detectors (e.g., fluorescence, phosphorescence or Raman scattering detectors), magnetic detectors, paramagnetic detectors, and other suitable detectors. The detectors may include suitable lamps, circuitry, monochromators, gratings, and the like to permit analysis of samples at a selected wavelength or in a desired manner.

In certain embodiments, a kit comprising a flow cell comprising a first port configured to provide fluidic coupling between the flow cell and a sample introduction device, and a fluid flow line configured to be coupled to the first port of the flow cell and sized and arranged to be placed between the flow cell and the sample introduction device to provide a sample of known viscosity to the flow cell from the sample introduction device at a selected time is provided. The fluid flow line of the kit is equivalent to the timing line described herein. Where the kit includes a plurality of different sized timing lines, the kit may include a suitable algorithm showing the relationship between fill time and reference time for each of the timing lines of the kit. A user can select or use the particular fill algorithm associated with the particular selected timing line.

In some examples, the kit can also include a sensor configured to be coupled to the first port of the flow cell to detect arrival of the sample at the flow cell. For example, the kit can include an ultrasonic sensor, an optical sensor, a magnetic sensor or other suitable sensors. If desired, the sensor can be configured to engage the first port of the flow cell through a friction fit, snap fit or other suitable connection. The sensor may also include suitable electrical connections for electrically coupling the sensor to a processor so that signals from the sensor can be received by the processor and used by the processor in determining whether direct or vacuum assisting filling is desired. In other embodiments, the kit can also include a valve configured to provide fluidic coupling between the flow cell and a pressure device in a second state of the valve and configured to provide fluidic decoupling between the flow cell and the pressure device in a first state of the valve. Illustrative valves include 3-ways valves, solenoid valves and other types of valves that can be actuated between an open and a closed position. In some embodiments, more than a single valve can be used in the kits or the systems described herein. In other examples, the kit can include a pressure device configured to provide a negative pressure in the flow cell when the valve is in the second state. For example, the pressure device can take the form of a pump in combination with a pressure chamber. The pump can be used to reduce the pressure in the pressure chamber to a desired negative pressure prior to or during filling of the flow cell. In some embodiments, the pump can be configured to pump for a pre-set period, e.g., 2 seconds, such that the pressure in the pressure chamber will be substantially constant from analysis to analysis. In other embodiments, the pressure chamber can include one or more pressure sensors configured to provide a measure of the actual pressure in the pressure chamber, and the pump can be configured to pump until a selected pressure in the pressure chamber is achieved. In other embodiments, the kit can include a reservoir comprising a cleaning or wash fluid. As described herein, the wash fluid can be used with the pressure system to introduce a turbulent flow of wash fluid into the flow cell to clean the flow cell between samples.

In certain embodiments, the devices described herein can be used as a downhole tool for measuring samples of varying viscosities during a drilling operation or oil or natural gas exploration operation. For example, a downhole tool comprising a flow cell comprising a fluid inlet, a sensor coupled to the fluid inlet of the flow cell and configured to determine the time of arrival of sample at the fluid inlet of the flow cell, a valve fluidically coupled to the flow cell, and a pressure device fluidically coupled to the flow cell when the valve is in a second state and fluidically decoupled from the flow cell when the valve is in a first state, the pressure device configured to provide a negative pressure to the flow cell when the valve is in the second state can be used to sample fluids during a drilling operation. In certain embodiments, the active filling function of the tool permits rapid filling and analysis of many different types of species that tend to be present in oil formations without having to use different instruments or different flow cells or analyze samples uphole.

In some embodiments, the flow cell is fluidically coupled to a fluid flow line between a sample introduction device and the flow cell, in which the fluid flow line is sized and arranged to provide a reference sample from the sample introduction device to the flow cell at a reference time. By providing a reference sample, the relationship between the fill time and the reference time may be periodically verified, if desired. In some embodiments, the tool can be configured to actuate the valve from the first state to the second state if arrival of the sample at the fluid inlet is greater than the threshold arrival time. In certain examples, the sensor of the tool can be an ultrasonic sensor, an optical sensor, a magnetic sensor or other suitable sensors. In some embodiments, the tool can include a detector or be electrically coupled to a detector or components thereof to analyze any sample in the flow cell. For example, an infrared detector, a fluorescence detector, a visible light detector or an ultraviolet light detector can be used to analyze the sample in the flow cell. The pressure device of the tool can be configured to provide a negative pressure of about −100 mbar or less, e.g., about −200 mbar or less or about −300 mbar or less. If desired, the entire tool may be enclosed in a chamber or housing to account for the increased pressures commonly present in downhole situations. In some embodiments, the tool can include a reservoir comprising a cleaning fluid, in which the reservoir is fluidically coupled to the flow cell, to permit cleaning of the tool downhole and without the need to remove the tool from the wellbore. In some embodiments, the pressure device can be configured to provide a negative pressure less than −500 mbar during introduction of the cleaning fluid to provide a turbulent flow of cleaning fluid to the flow cell.

In certain embodiments, the devices described herein can be used in methods to accelerate flow of sample into a flow cell. For example, a method comprising actuating a valve between a flow cell and a pressure device from a first state to a second state to provide fluidic coupling between the flow cell and the pressure device if a sensed time of sample arrival at the sample cell is greater than a threshold value can be used to fill a flow cell with a viscous fluid. In some embodiments, the method can include providing a negative pressure using the pressure device to accelerate the sample into the sample cell. In other embodiments, the method can include configuring the negative pressure to be about −100 mbar or less, e.g., −300 mbar or less. In certain embodiments, the method can include providing a fluid flow line configured to be placed between a sample introduction device and the flow cell, in which the fluid flow line is sized and arranged to provide a reference sample from the sample introduction device to the flow cell at a reference time. In additional embodiments, the fluid flow line can be configured to be about 10 inches long. In some embodiments, the method can include detecting arrival of sample at the flow cell using an ultrasonic sensor or an optical sensor or other suitable sensor. In certain examples, the method can include analyzing sample in the flow cell using an infrared detector or other suitable detector.

In certain examples, the method can include measuring the time of arrival of the sample at the flow cell and fluidically coupling the flow cell to the pressure device if the arrival time is greater than a threshold time. In other examples, the method can include measuring the time of arrival of the sample at the flow cell and operating the flow cell in a fluidically decoupled state if the arrival time is less than a threshold time. In some embodiments, the method can include providing a turbulent flow of a cleaning fluid to the flow cell to remove any residue from the flow cell.

In certain embodiments, a method comprising providing a negative pressure from a pressure device fluidically coupled to the flow cell to accelerate filling of the flow cell with the sample can be used to fill a flow cell with a sample. In some examples, the method can include introducing sample from a sample introduction device into the flow cell fluidically coupled to the sample introduction device, the flow cell comprising a sensor in a fluid inlet, in which the sensor is configured to detect arrival of the sample at the flow cell. In other examples, the method can include actuating a valve between the pressure device and the sample cell to a position that provides the fluidic coupling between the pressure device and the sample cell if the detected time of sample arrival at the sample cell is greater than a threshold value. In additional examples, the method can include configuring the negative pressure to be about −100 mbar or less. In further examples, the method can include providing a fluid flow line configured to be placed between a sample introduction device and the flow cell, in which the fluid flow line is sized and arranged to provide a reference sample from the sample introduction device to the flow cell at a reference time. In some examples, the method can include detecting arrival of sample at the flow cell using an ultrasonic sensor or an optical sensor or other suitable sensor. In certain embodiments, the method can include analyzing sample in the flow cell using an infrared detector or other suitable detector.

In some embodiments, the method can include measuring the time of arrival of the sample at the flow cell and fluidically coupling the flow cell to the pressure device if the arrival time is greater than a threshold time. In certain embodiments, the method can include measuring the time of arrival of the sample at the flow cell and operating the flow cell in a fluidically decoupled state if the arrival time is less than a threshold time. In further embodiments, the method can include providing a turbulent flow of a cleaning fluid to the flow cell to remove any residue from the flow cell.

In certain examples, a method of loading a flow cell at a selected flow rate where samples of varying viscosity are loaded comprises measuring the arrival time of a sample at an entrance port of the flow cell, and fluidically coupling the flow cell to a pressure device providing a negative pressure to accelerate filling of the flow cell to the selected flow rate if the measured arrival time exceeds a threshold value can be used to fill a flow cell. In some embodiments, the method can include measuring the arrival time of the sample using an ultrasonic sensor. In additional embodiments, the method can include measuring the arrival time of the sample using an optical sensor or other suitable sensor. In some embodiments, the method can include actuating a 3-way solenoid valve to a second state to provide the fluidic coupling between the flow cell and the pressure device. In certain examples, the method can include adjusting the negative pressure to be about −100 mbar or less, e.g., −200 mbar or −300 mbar. In some embodiments, the method can include providing a fluid flow line configured to be placed between a sample introduction device and the flow cell, in which the fluid flow line is sized and arranged to provide a reference sample from the sample introduction device to the flow cell at a reference time. In certain examples, the method can include providing the negative pressure from a pressure device comprising a pressure chamber with a volume at least thirty times larger than the volume of the flow cell. In additional examples, the method can include providing a selected negative pressure to the flow cell during filling of the flow cell. In some embodiments, the method can include introducing a turbulent flow of a cleaning fluid into the flow cell to remove any residual sample from the flow cell. In further embodiments, the method can include configuring the negative pressure to be less than −500 mbar during introduction of the cleaning fluid.

Certain specific examples are described below to illustrate further some of the novel aspects and embodiments of the technology described herein.

Example 1

Figure 5:
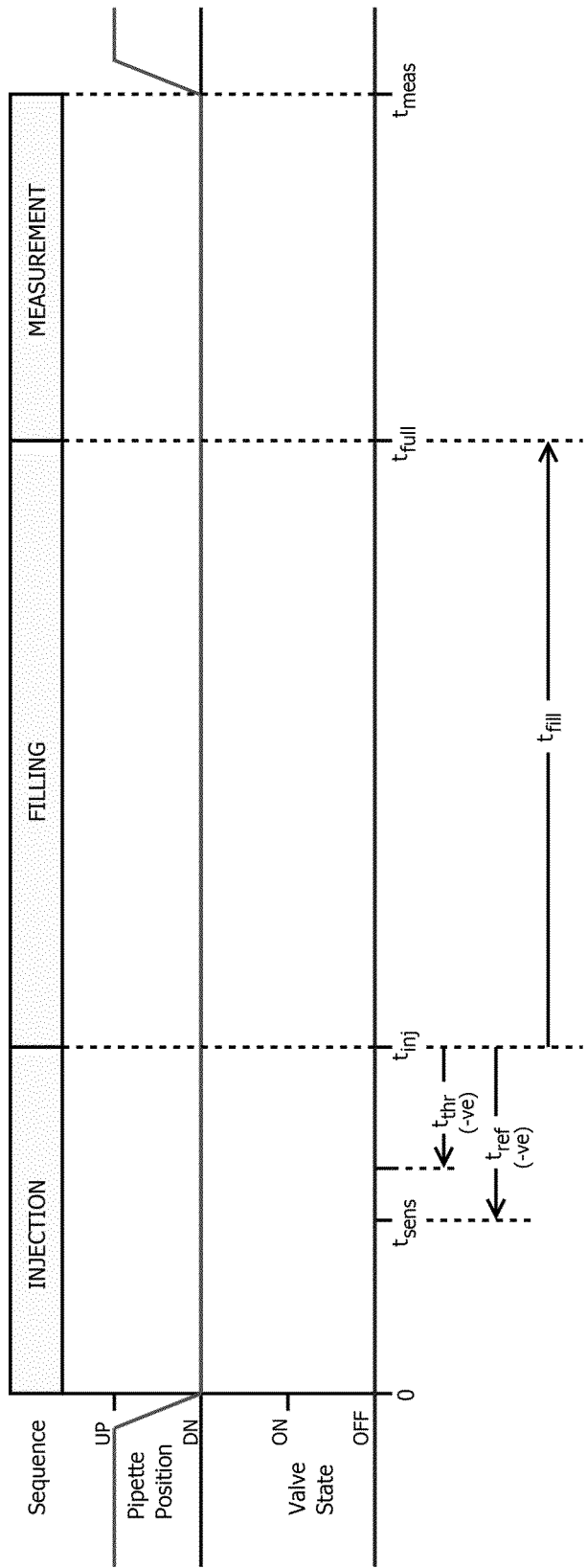
FIG. 5 is a timing diagram for passive operation, e.g., direct filling, of a system as described herein, in accordance with certain examples.
Figure 6:
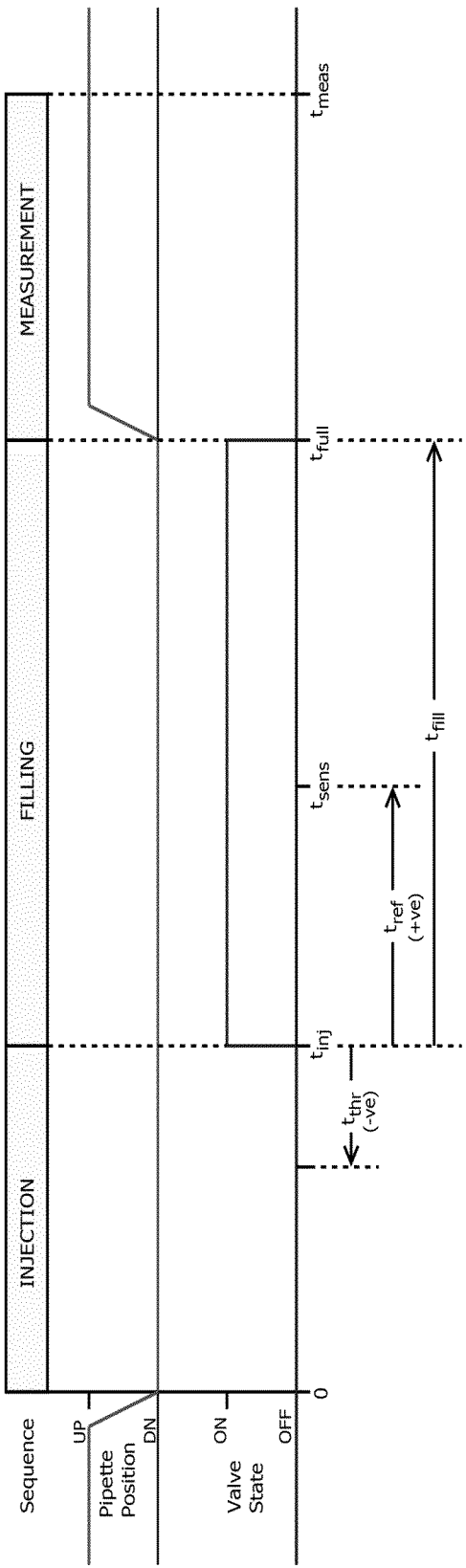
FIG. 6 is a timing diagram for active operation, e.g., vacuum assisted filling, of a system as described herein, in accordance with certain examples.

Referring to the system of FIG. 4 and the timing diagrams shown in FIGS. 5 and 6, one embodiment of a sample cell filling procedure is described as follows: the three wave valve 440 is set to the OFF condition (com is connected to n.o.) so that the fluid circuit between the fill cup 410 and the three way valve 440 is at zero gauge pressure (atmosphere). The pressure chamber 450, having a volume of about 125 mL, is pumped down for a fixed period of time. This presets the chamber 450 to a known (negative) gauge pressure. Generally, about −216 mbar, −311 mbar and −439 mbar of pressure can be reached when the pump time is 1 second, 2 seconds and 3 seconds, respectively; this pressure is locked in the chamber. The pipette tip 470 descends into the fill cup 410 where it makes a seal. The syringe of the pipette tip 470 displaces a fixed volume of system fluid, compressing the air pocket in the pipette tip behind the sample. This volume displaced is sufficient to fill the fluid circuit with sample from the fill cup 410 to the probed region of the flow cell 430. The sensor 420 is polled continuously and if it triggers (sample detected) the time of triggering is recorded ($t_{sens}$). The system waits for the sample injection to complete and when it completes (syringe stops) the time ($t_{inj}$) is recorded. If the sensor 420 has already triggered then the reference time is calculated: ($t_{ref}=t_{sens}-t_{fill}$) (the value will be negative). If ($t_{ref} \geq t_{thr}$) (a pre-determined threshold value) or the sensor has not yet triggered, then the fill mode is set to 'vac assist'. Otherwise the fill mode is set to direct. If the fill mode='vac assist', the three way valve 440 is set to the ON state (com connected to n.c.) causing a sudden pressure drop in front of the sample fluid column (see FIG. 6). This accelerates the flow of sample through the system. If the fill mode='direct', the valve 440 remains OFF (see FIG. 5) and the sample continues propelled only by the positive air pressure in the tip of the pipette 470 behind the sample. If the sample sensor has not yet triggered it is polled until sample is detected. The time of detection ($t_{sens}$) is recorded and ($t_{ref}=t_{sens}-t_{inj}$) is calculated (the value will be positive).

As described herein, the fill time ($t_{fill}$) is computed from the reference time ($t_{ref}$), the functional relationship between ($t_{ref}$) and ($t_{fill}$) having been determined in advance. A different function is used for 'direct' and 'vac assist' filling modes. A simple linear relationship or a non-linear relationship can be used to model the relationship between $t_{fill}$ and $t_{ref}$.

As soon as the fill time ($t_{fill}$) has elapsed, the three way valve 440 is switched to the OFF state (it will already be OFF in 'direct' mode). This sets the gauge pressure in front of the sample column to zero (atmosphere) and halts the fluid motion. At this point the cell 430 has been filled with sample. If the fill mode=vac assist, the tip of the pipette 470 is lifted from the cup 410. If the fill mode=direct, the tip of the pipette 470 stays down in the cup 410. This prevents movement of the fluid column for low viscosity samples. The sample is then measured using a suitable detector, e.g., a FTIR detector.

Example 2

To wash the flow cell and remove any residual sample between sample runs, the following procedure can be used: the three way valve 440 is set the ON state and the pressure chamber 450 is pumped continuously. This pumping pulls sample out of the flow cell 430 towards the pressure chamber 450. The system waits until the sample column breaks ups (cavitation). The required volume of cleaning solvent is calculated from the value of ($t_{ref}$). This volume is injected (in a series of shots or aliquots) from a position just above the fill cup 410 (i.e. no seal is made between the fill cup 410 and the pipette 470) and is pulled through the fluid circuit under vacuum into the pressure chamber 450. The flow is highly turbulent and efficiently cleans the cell. The vacuum is maintained for a sufficient time to dry the fluid circuit in preparation for the next sample.

Example 3

A series of known samples were used to determine the relationship between the reference time and the fill time. The samples had viscosities that varied from 30 cSt (@ 40° C.) to 940 cSt (@ 40° C.). An OilExpress system commercially available from PerkinElmer Environmental Sciences, Inc. was modified to include the assembly shown in FIG. 4. A prepump time of 2 seconds was used to reduce the pressure in the pressure chamber to about −311 mbar.

Figure 7:
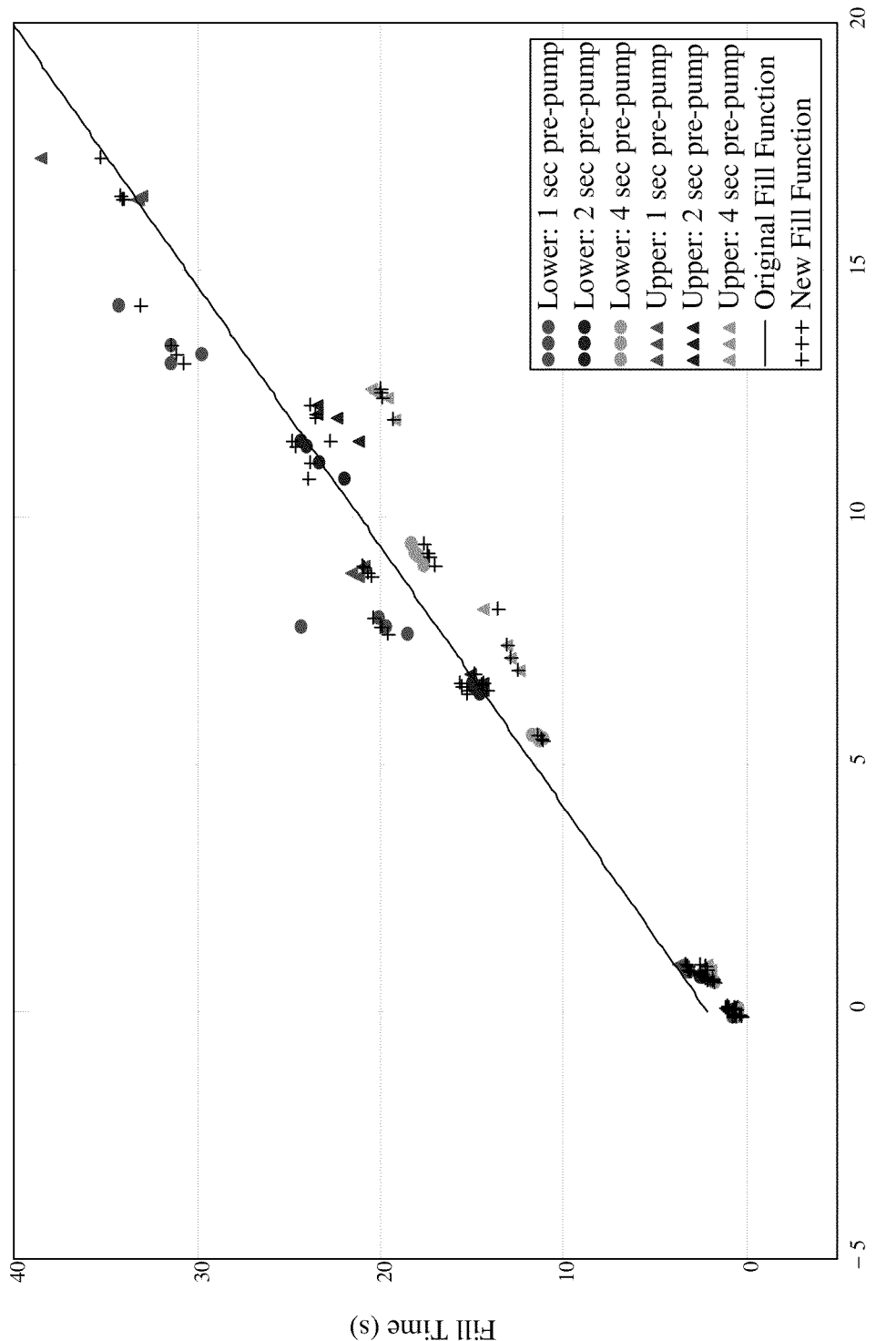
FIG. 7 is a graph showing the relationship of fill time and reference time for a series of measured samples, in accordance with certain examples.

The results are shown graphically in FIG. 7. The original fill function refers to a linear fit (Equation [1]) whereas the new fill function refers to a non-linear fit (Equation [2]). As shown in FIG. 5, the new fill function provides a better approximation of the relationship between the reference time and the fill time. A fit of the data, using Equation [2], was used to determine Equation [6] for the fill time for active or vacuum assisted filling of the flow cell. The vacuum assisted filling algorithm for the filling time T was determined to be $$T = (1423 + kt_{ref} - 2.882 \times 10^{-5} t_{ref} + 2.143 P + 2.491 \times 10^{-3} t_{ref} P) \times 1.3 + t_{ref} \quad [6]$$

where the value of k was 2.2 if the flow cell was in the lower spectrometer position, and the value of k was 2.0 if the flow cell was in the upper spectrometer position. For comparison, a linear fit, based on Equation [1], provided an equation of $T = 1.9 t_{ref} + 2.083$.

Where direct or passive filling of the flow cell was used, a fit of the data was used to determine Equation [7]. The direct filling algorithm for the filling time T was determined to be $$T = 8 t_{ref} + 6500 + \text{FillOffset} \quad [7]$$

where the FillOffset value was 1000 if the fill time was less than or equal to 1000 ms. The direct fill time was the same for the upper and lower positions and did not depend on the chamber pre-pressure.

Example 4

The system of FIG. 4 was used to test various hydrocarbon fluids. It was tested with oil samples having viscosities ranging from 10 cSt up to 680 cSt (at 40° C.) and with heptane samples having a viscosity of 0.5 cSt. The fill times achieved for the various samples are shown in the table of FIG. 8. As shown in the table, when active or vacuum assisted (Vac Assist) filling is used, fluids having viscosities above 30 cSt can be loaded into a chamber at substantially similar fill times as a fluid having a viscosity of about 8.848 cSt. Where viscosity increases from about 30 cSt to about 120 cSt, the fill time using vacuum assisted filling increased by less than 2 seconds. Where viscosity increases from about 30 cSt to about 315 cSt, the fill time increases only by about 5 seconds. Where viscosity increases from 30 cSt to about 680 cSt, fill time increases by only about 15 seconds. By using active filling with high viscosity fluids, the filling time of the flow cell can be reduced substantially.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A system configured to accelerate viscous sample flow into a flow cell, the system comprising:
   a sample introduction device configured to provide a positive pressure;
   a flow cell fluidically coupled to the sample introduction device and configured to receive sample under the positive pressure from the sample introduction device through a fluid inlet of the flow cell;
   a timing fluid line between the sample introduction device and the fluid inlet of the flow cell, the timing fluid line sized and arranged to provide a reference sample from the sample introduction device to the flow cell at a reference time;
   a sensor fluidically coupled to the timing fluid line and at the fluid inlet of the flow cell, the sensor configured to determine a time of arrival of the sample;
   a valve fluidically coupled to the flow cell at an outlet of the flow cell; and
   a pressure device fluidically coupled to the valve downstream of the valve, the pressure device configured to provide a negative pressure to the flow cell when the valve is in a second state to accelerate flow of the sample into the flow cell and configured to be fluidically decoupled from the flow cell when the valve is in a first state to permit sample to flow into the flow cell under the positive pressure provided by the sample introduction device.

2. The system of claim 1, in which the pressure device comprises a pressure chamber configured to provide a negative pressure to the flow cell when the valve is in the second state and fluidically decoupled from the cell when the valve is in the first state.

3. The system of claim 2, in which the pressure device further comprises a pump configured to provide the negative pressure in the pressure chamber.

4. The system of claim 1, further comprising a processor electrically coupled to the valve and the sensor and configured to switch the state of the valve between the first state and the second state based on a determined fill time of the sample.

5. The system of claim 4, in which the processor is configured to switch the valve from the first state to the second state if the determined fill time exceeds a threshold value.

6. The system of claim 4, in which the processor is configured to maintain the valve in the first state if the determined fill time is below a threshold value to permit sample to flow into the flow cell only under the positive pressure provided from the sample introduction device.

7. The system of claim 1, further comprising a detector configured to detect sample in the flow cell.

8. The system of claim 1, further comprising a reservoir comprising a cleaning fluid, in which the reservoir is fluidically coupled to the flow cell.

9. The system of claim 6, in which the processor is configured to determine the fill time for the sample using Equation [2]

$$T=(C_1+kx-C_2x^2+C_3P+C_4xP) \times z+x \quad [2]$$

where $C_1$, $C_2$, $C_3$ and $C_4$ are constants determined empirically from a graph of fill times versus reference times, k is a constant, x is a reference time, P is a pressure device pressure in mbar before a dispense operation is initiated and z is a fill factor.

10. The system of claim 1, in which the valve is configured as a 3-way solenoid valve.

11. The system of claim 1, in which the sensor comprises an ultrasonic sensor.

12. A system comprising a flow cell fluidically coupled to a valve downstream of the flow cell and to a pressure device downstream of the valve, the flow cell fluidically coupled to the pressure device when the valve is in a second state to accelerate sample into an inlet of the flow cell, in which the flow cell is fluidically decoupled from the pressure device when the valve is in a first state to permit sample to flow into the flow cell under positive pressure without acceleration of the sample into the flow cell, a sensor positioned at the inlet of the flow cell and configured to determine a time of arrival of the sample at the sensor, a processor electrically coupled to the sensor and configured to determine if the valve should be switched from the first state to the second state using a reference time and a time of arrival of the sample at the sensor, and a fluid flow line fluidically coupled to the inlet of the flow cell, in which the fluid flow line is sized and arranged to provide a reference sample to the flow cell at a reference time.

13. The system of claim 12, in which the pressure device comprises a pressure chamber fluidically coupled to the flow cell when the valve is in the second state and fluidically decoupled from the flow cell when the valve is in the first state.

14. The system of claim 13, in which the pressure device further comprises a pump configured to provide the negative pressure in the pressure chamber.

15. The system of claim 12, in which the processor is configured to determine a fill time for the sample using Equation [2]

$$T=(C_1+kx-C_2x^2+C_3P+C_4xP) \times z+x \quad [2]$$

where $C_1$, $C_2$, $C_3$ and $C_4$ are constants determined empirically from a graph of fill times versus reference times, k is a constant, x is a reference time, P is a pressure device pressure in mbar before a dispense operation is initiated and z is a fill factor.

16. The system of claim 15, in which the processor is configured to switch the valve from the first state to the second state if the determined fill time exceeds a threshold value.

17. The system of claim 15, in which the processor is configured to maintain the valve in the first state if the determined fill time is below a threshold value.

18. The system of claim 12, further comprising a detector configured to detect sample in the flow cell.

19. The system of claim 12, further comprising a reservoir comprising a cleaning fluid, in which the reservoir is fluidically coupled to the flow cell.

20. The system of claim 12, in which the valve is configured as a 3-way solenoid valve.

21. The system of claim 12, in which the sensor comprises an ultrasonic sensor.

* * * * *